(12) United States Patent
Tanaka

(10) Patent No.: US 8,285,016 B2
(45) Date of Patent: Oct. 9, 2012

(54) ENDOSCOPE INSERTION DIRECTION DETECTING DEVICE AND ENDOSCOPE INSERTION DIRECTION DETECTING METHOD

(75) Inventor: Hideki Tanaka, Tama (JP)

(73) Assignee: Olympus Medical System Corp., Tokyo (JP)

(*) Notice: Subject to any disclaimer, the term of this patent is extended or adjusted under 35 U.S.C. 154(b) by 1027 days.

(21) Appl. No.: 12/253,707

(22) Filed: Oct. 17, 2008

(65) Prior Publication Data

US 2009/0041320 A1 Feb. 12, 2009

Related U.S. Application Data

(63) Continuation of application No. PCT/JP2007/053587, filed on Feb. 27, 2007.

(30) Foreign Application Priority Data

Apr. 17, 2006 (JP) .................................. 2006-113794

(51) Int. Cl.
*G06K 9/00* (2006.01)

(52) U.S. Cl. ........................................ 382/128; 382/224

(58) Field of Classification Search .................. 382/128, 382/209, 100, 106, 133, 168; 600/117, 118, 600/109, 103; 345/424
See application file for complete search history.

(56) References Cited

U.S. PATENT DOCUMENTS

| 4,916,533 | A * | 4/1990 | Gillies et al. ..................... 348/65 |
| 5,036,464 | A * | 7/1991 | Gillies et al. .................... 600/145 |
| 7,258,664 | B2 * | 8/2007 | Nishimura et al. ........... 600/117 |
| 7,599,533 | B2 * | 10/2009 | Nishimura et al. ........... 382/128 |
| 7,857,752 | B2 * | 12/2010 | Hasegawa et al. ............ 600/109 |
| 8,062,210 | B2 * | 11/2011 | Uchiyama et al. ............ 600/103 |
| 8,211,009 | B2 * | 7/2012 | Tanaka et al. ................. 600/117 |
| 8,212,862 | B2 * | 7/2012 | Kase et al. ....................... 348/68 |
| 2005/0010082 | A1 * | 1/2005 | Nishimura et al. ........... 600/145 |

FOREIGN PATENT DOCUMENTS

| EP | 1 437 083 A1 | 7/2004 |
| JP | 2680111 B2 | 8/1997 |
| JP | 2710384 | 10/1997 |
| JP | 2002-165757 | 6/2002 |
| JP | 2002165757 | * 6/2002 |
| JP | 2003-093328 | 4/2003 |
| JP | 2004-167010 | 6/2004 |
| WO | WO 03/026497 A1 | 4/2003 |

OTHER PUBLICATIONS

Hasegawa, O., "Pattern Recognition for Understanding of Scene," O Plus E, Oct. 2003, pp. 1130-1136.
Abstract Only of Japanese Patent Application Publication No. 02-182231 dated Jul. 16, 1990.
Abstract Only of Japanese Patent Application Publication No. 02-140134 dated May 29, 1990.
International Search Report dated Mar. 27, 2007.

* cited by examiner

*Primary Examiner* — Wesley Tucker
*Assistant Examiner* — Nancy Bitar
(74) *Attorney, Agent, or Firm* — Scully, Scott, Murphy & Presser, P.C.

(57) ABSTRACT

An endoscope insertion direction detecting device includes a classification section for performing, on a scene of an endoscope image of a moving image picked up by an endoscope inserted into a body cavity, classification into classes for a plurality of different feature values relating to detection of an endoscope insertion direction in the body cavity; and an insertion direction computing section, provided for each of the classes for the feature values, into which the classification is performed, for computing an insertion direction of the endoscope.

14 Claims, 15 Drawing Sheets

| | | | | | | |
|---|---|---|---|---|---|---|
| No.1 | No.2 | No.6 | No.10 | No.14 | No.18 | No.22 |
| No.3 | No.7 | No.11 | No.15 | No.19 | No.23 | |
| No.4 | No.8 | No.12 | No.16 | No.20 | No.24 | |
| No.5 | No.9 | No.13 | No.19 | No.21 | No.25 | |

| a11 | a12 | a13 |
|---|---|---|
| a21 | a22 | a23 |
| a31 | a32 | a33 | a22 + a23

| a12 | a13 | a14 |
|-----|-----|-----|
| a22 | a23 | a24 |
| a32 | a33 | a34 | a23 + a24

RESOLUTION A

RESOLUTION B

FIG.22
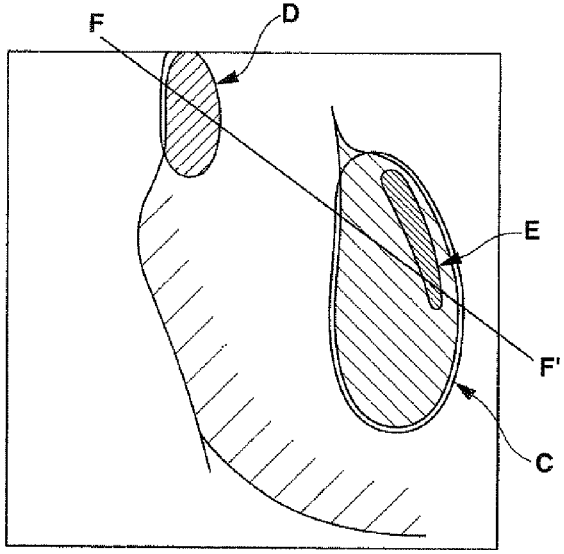
FIG.23
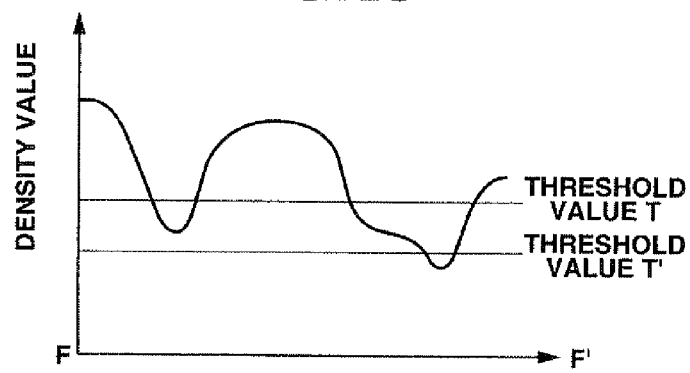
FIG.24
| b11 | b21 | b31 | b41 |
|-----|-----|-----|-----|
| b12 | b22 | b32 | b42 |
| b13 | b23 | b33 | b43 |
| b14 | b24 | b34 | b44 |

ENDOSCOPE INSERTION DIRECTION DETECTING DEVICE AND ENDOSCOPE INSERTION DIRECTION DETECTING METHOD

CROSS REFERENCE TO RELATED APPLICATION

This application is a continuation application of PCT/JP2007/053587 filed on Feb. 27, 2007 and claims benefit of Japanese Application No. 2006-113794 filed in Japan on Apr. 17, 2006, the entire contents of which are incorporated herein by this reference.

BACKGROUND OF THE INVENTION

1. Field of the Invention

The present invention relates to an endoscope insertion direction detecting device for detecting an insertion direction of an endoscope and an endoscope insertion direction detecting method.

2. Description of the Related Art

Endoscopes have recently been in wide use in the field of medicine. In an endoscopic examination which is performed by inserting an insertion portion of an endoscope into a body cavity, smooth insertion into an intricately curved part such as a large intestine may require a lot of skill.

For the reason, a configuration which enables even an inexperienced surgeon to easily insert an insertion portion can reduce time required for an endoscopic examination and offers major benefits.

For example, Japanese Patent Application Laid-Open Publication No. 2004-167010 as a first conventional example discloses an endoscope insertion direction detecting device including pixel extraction means for extracting a pixel with a predetermined density value, such as a halation relating to detection of an endoscope insertion direction or a luminal structure, from an endoscope image. The first conventional example determines an endoscope insertion direction on the basis of an extraction result.

Japanese Patent Application Laid-Open Publication No. 2003-93328 as a second conventional example discloses an endoscope insertion direction detecting device and an endoscope insertion direction detecting method for determining a direction in which an insertion portion of an endoscope is to be inserted by detecting a light-dark direction in an endoscope image.

SUMMARY OF THE INVENTION

An endoscope insertion direction detecting device according to the present invention includes: a classification section for performing, on a scene of an endoscope image of a moving image picked up by an endoscope inserted into a body cavity, classification into classes for a plurality of different feature values relating to detection of an endoscope insertion direction in the body cavity; and an insertion direction computing section, provided for each of the classes for the feature values, into which the classification is performed by the classification section, for computing an insertion direction of the endoscope.

An endoscope insertion direction detecting method according to the present invention includes: a classification step of performing, on a scene of an endoscope image of a moving image picked up by an endoscope inserted into a body cavity, classification into classes for a plurality of different feature values relating to detection of an endoscope insertion direction in the body cavity; and an insertion direction computing step of computing, for each of the classes for the feature values, into which the classification is performed in the classification step, an insertion direction of the endoscope.

BRIEF DESCRIPTION OF THE DRAWINGS

FIG. 22 is a view schematically showing an endoscope image in which a dark section region or the like is coresident with a lumen dark section region, according to the third embodiment of the present invention;

FIG. 23 is a graph showing a density value along a section taken along line F-F' in FIG. 22 according to the third embodiment of the present invention;

FIG. 24 is a view showing small regions divided when a method in FIG. 21 is performed, according to the third embodiment of the present invention.

DESCRIPTION OF THE PREFERRED EMBODIMENT(S)

Embodiments of the present invention will be described below with reference to the drawings.

First Embodiment

Figure 1:
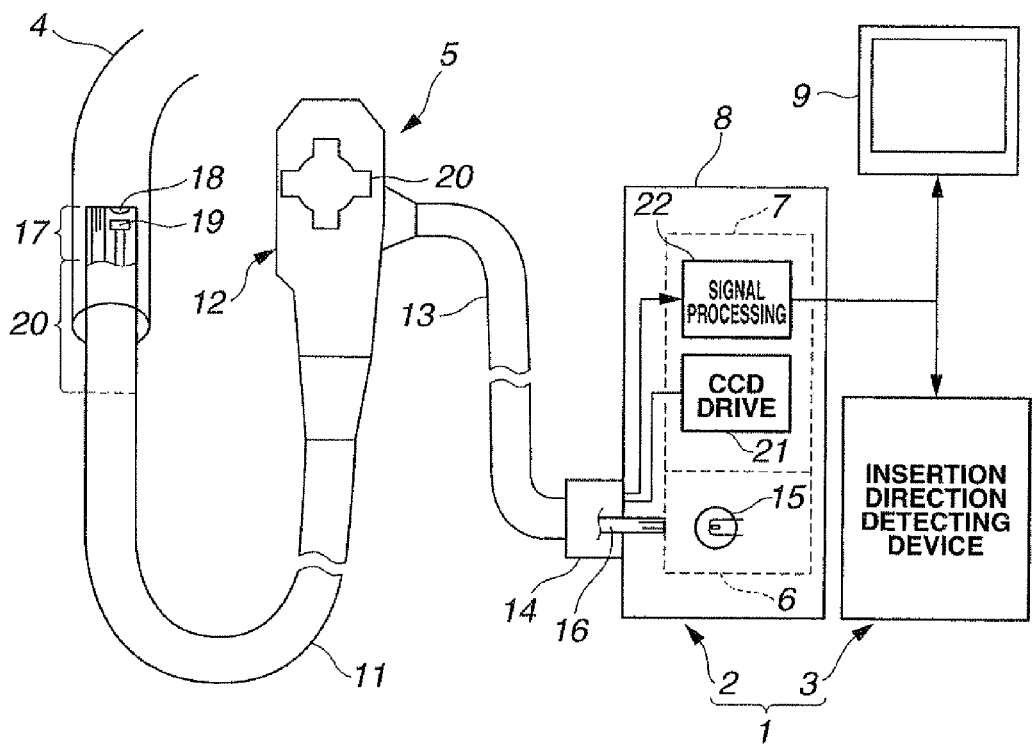
FIG. 1 is a view of an overall configuration of an endoscope system including an insertion direction detecting device according to a first embodiment of the present invention.
Figure 2:
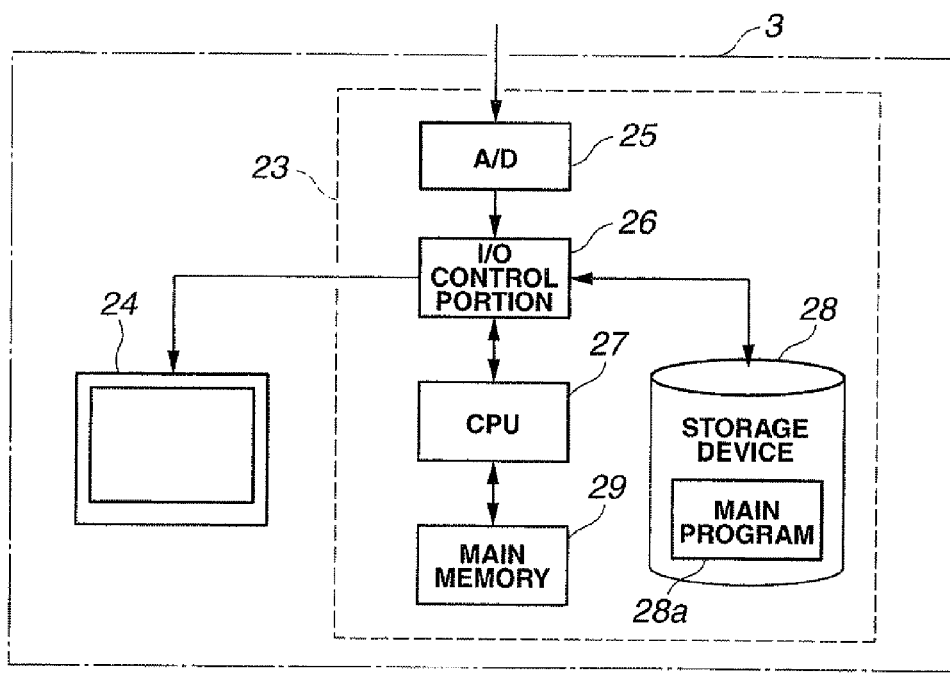
FIG. 2 is a block diagram showing a configuration of the insertion direction detecting device according to the first embodiment of the present invention.
Figure 3:
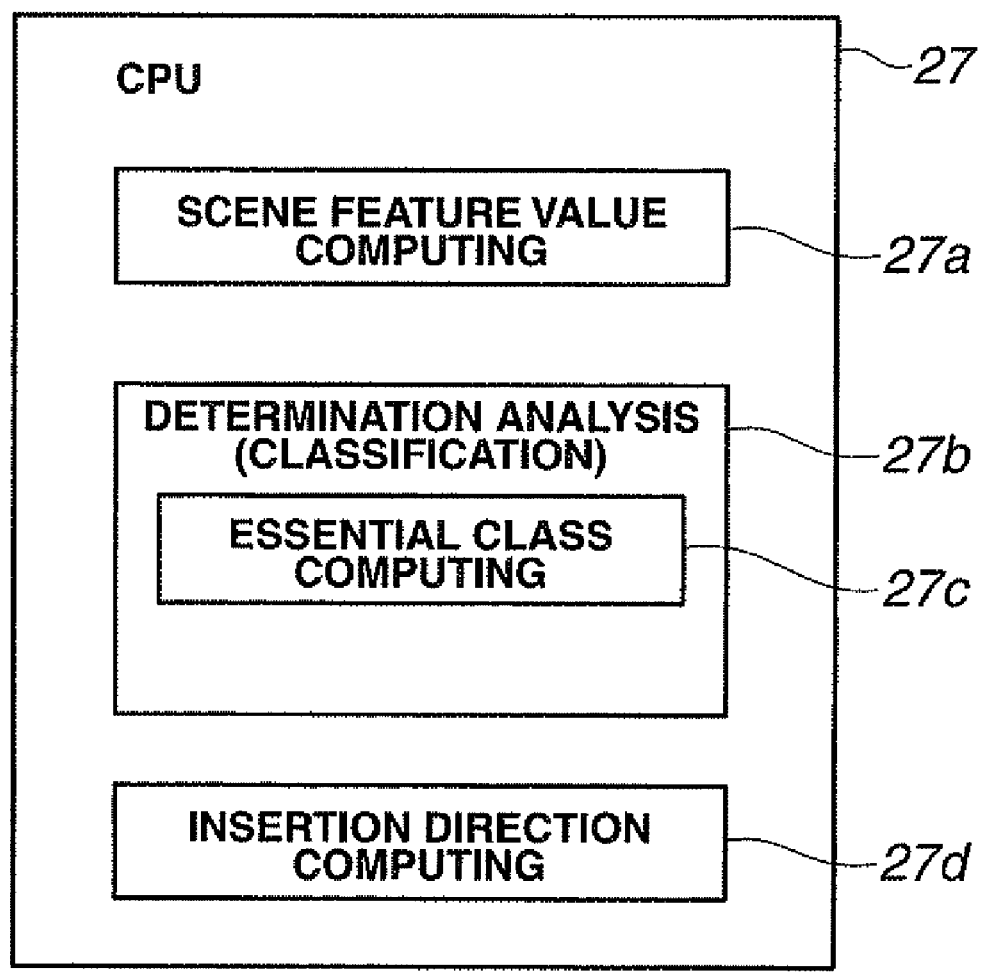
FIG. 3 is a diagram showing main facilities of a CPU constituting the insertion direction detecting device according to the first embodiment of the present invention.
Figure 4:
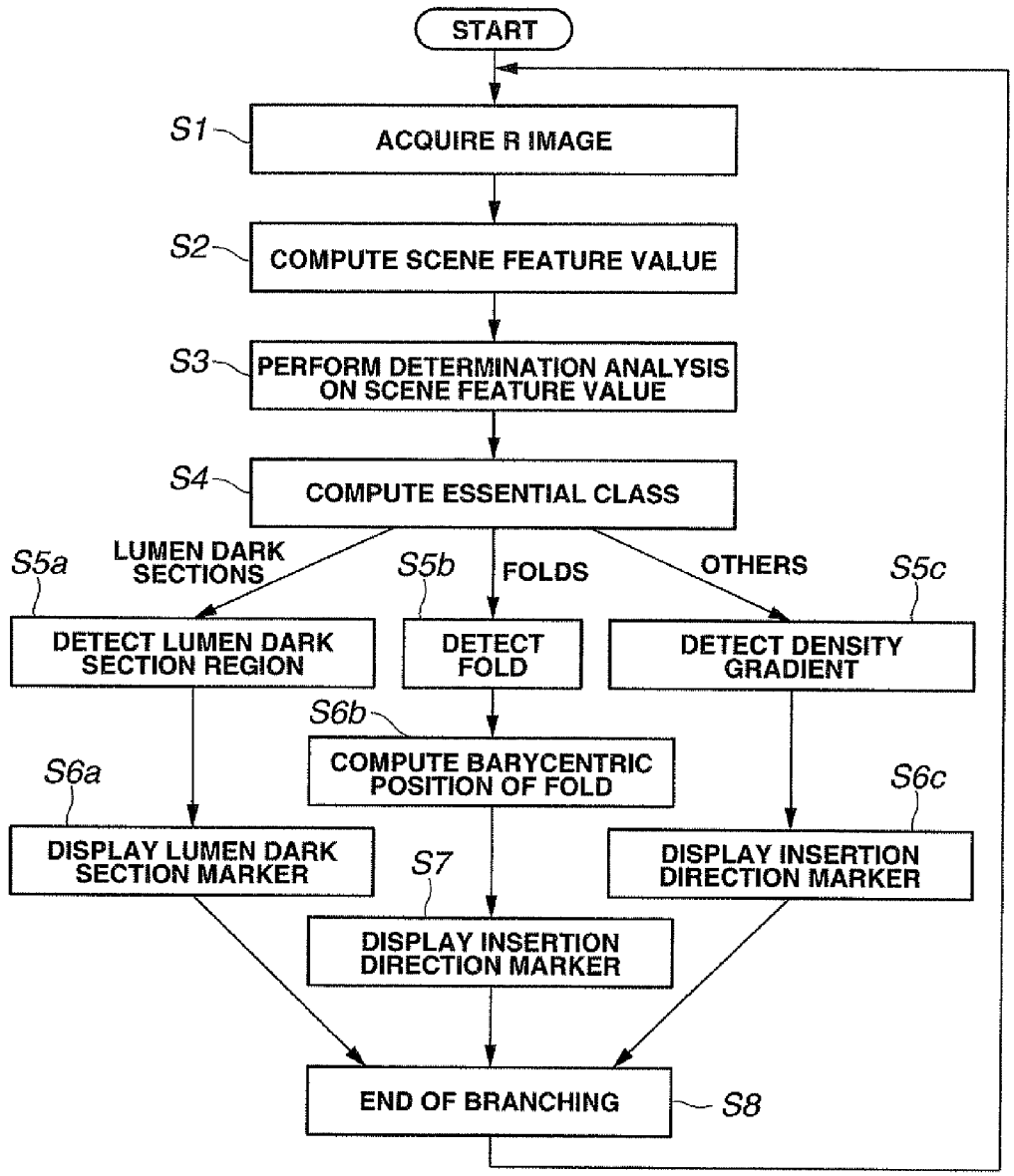
FIG. 4 is a flow chart showing an endoscope insertion direction detecting process according to the first embodiment of the present invention.
Figure 5:
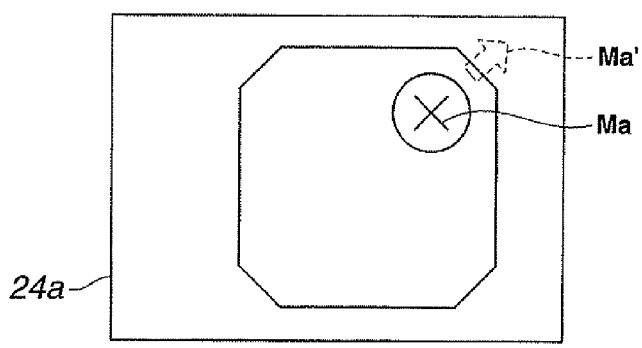
FIG. 5 is a view of an example in which a marker indicating a detected lumen dark section region is displayed on a display screen of an endoscope image, according to the first embodiment of the present invention.
Figures 6, 7, 8:
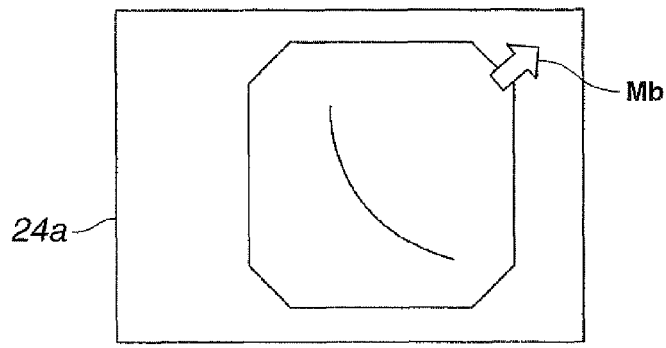
FIG. 6 is a view of an example in which an insertion direction marker indicating an insertion direction is displayed on the display screen of the endoscope image using a detected fold according to the first embodiment of the present invention.
FIG. 7 is a view showing two-dimensional patterns serving as a reference when a scene feature value is computed by using a higher order local autocorrelation coefficient, according to the first embodiment of the present invention.
FIG. 8 is a first view for explaining a computation for computing a scene feature value according to the first embodiment of the present invention.
Figures 9, 10:
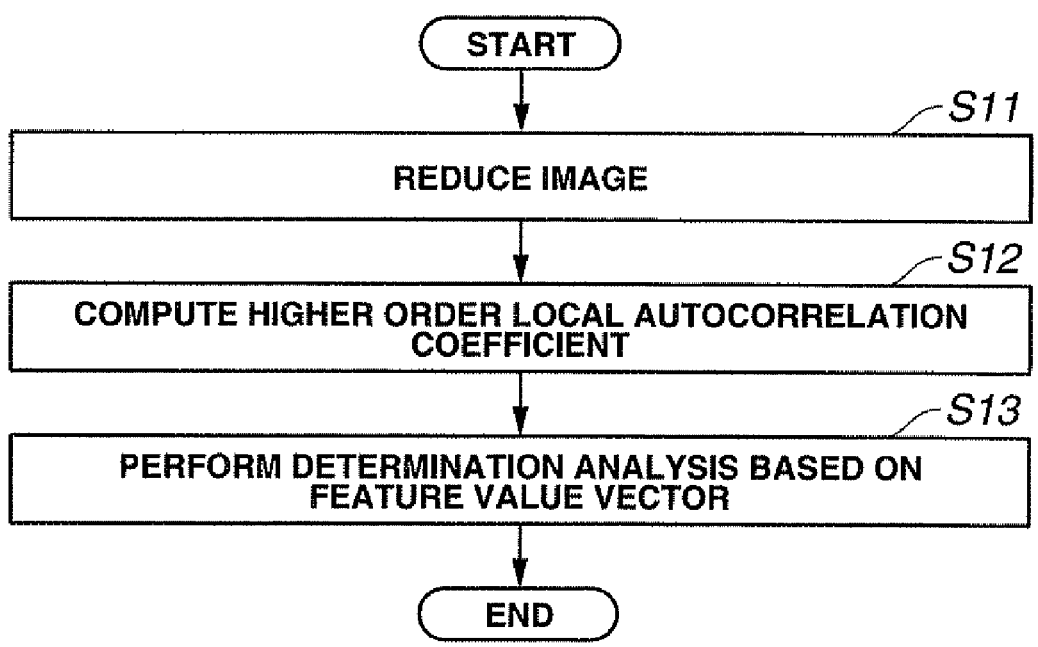
FIG. 9 is a second view for explaining a computation for computing a scene feature value according to the first embodiment of the present invention.
FIG. 10 is a flow chart showing a procedure for a process of computing a feature value according to the first embodiment of the present invention.
Figure 11:
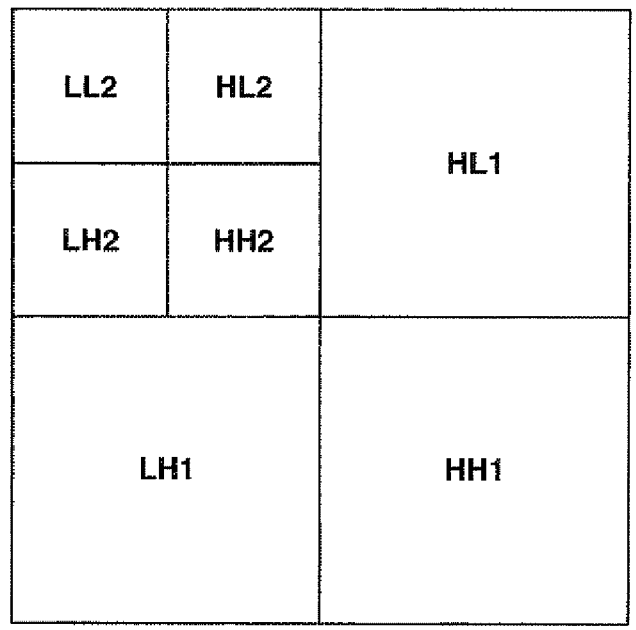
FIG. 11 is a view showing an example of subband images reduced by a discrete wavelet transform used at the time of image reduction in FIG. 10, according to the first embodiment of the present invention.
Figure 12:
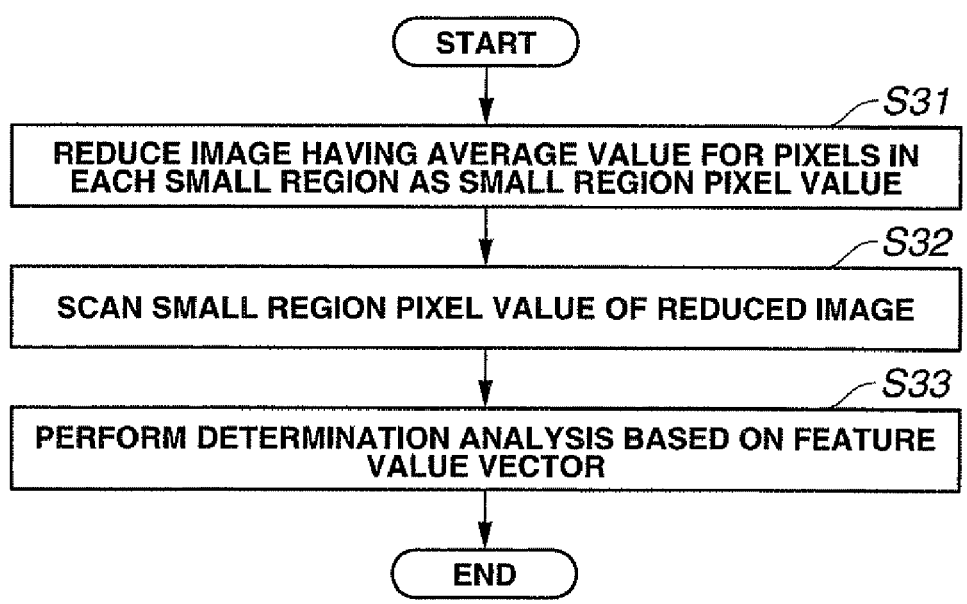
FIG. 12 is a flow chart showing a procedure for a process of computing a feature value according to a first modification of the first embodiment of the present invention.
Figure 13:
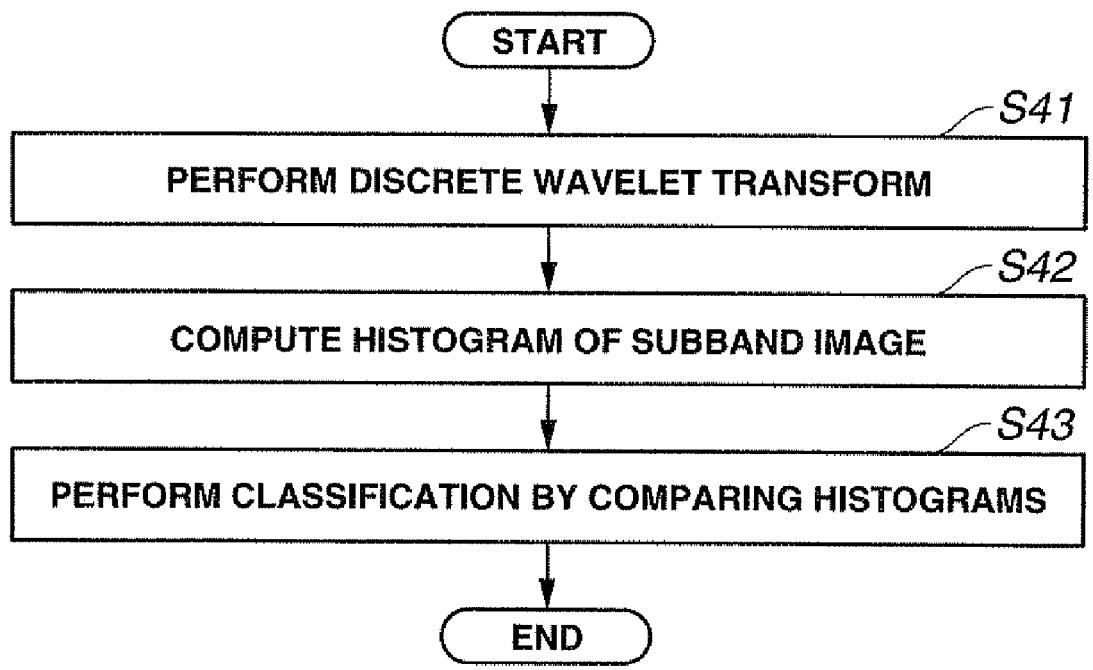
FIG. 13 is a flow chart showing a procedure for a process of computing a feature value according to a second modification of the first embodiment of the present invention.
Figure 14:
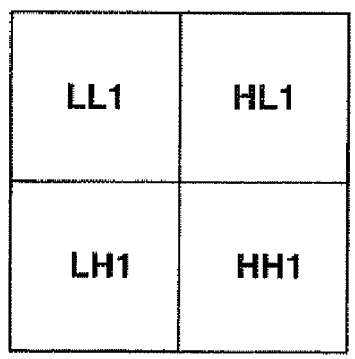
FIG. 14 is a view showing an example of subband images reduced by a discrete wavelet transform in FIG. 13, according to the second modification of the first embodiment of the present invention.

FIGS. 1 to 14 relate to a first embodiment of the present invention. FIG. 1 shows an overall configuration of an endoscope system including an insertion direction detecting device. FIG. 2 shows a configuration of the insertion direction detecting device. FIG. 3 shows main facilities of a CPU constituting the insertion direction detecting device. FIG. 4 shows an endoscope insertion direction detecting process. FIG. 5 shows an example in which a marker indicating a detected lumen dark section region is displayed on a display screen of an endoscope image. FIG. 6 shows an example in which an insertion direction marker indicating an insertion direction is displayed on the display screen of the endoscope image using a detected fold. FIG. 7 shows two-dimensional patterns serving as a reference when a scene feature value is used to compute a higher order local autocorrelation coefficient. FIGS. 8 and 9 show views for explaining computations for computing a scene feature value. FIG. 10 shows a procedure for a process of computing a feature value. FIG. 11 shows an example of subband images reduced by a discrete wavelet transform used at the time of image reduction in FIG. 10. FIG. 12 shows a procedure for a process of computing a feature value according to a first modification. FIG. 13 shows a procedure for a process of computing a feature value according to a second modification. FIG. 14 shows an example of subband images reduced by a discrete wavelet transform in FIG. 13.

As shown in FIG. 1, an endoscope system 1 according to the first embodiment of the present invention is composed of an endoscope device 2 and an endoscope insertion direction detecting device (hereinafter abbreviated as an insertion direction detecting device) 3 which performs image processing for detecting an insertion direction on a video signal of an endoscope image inputted from the endoscope device 2.

The endoscope device 2 is composed of an endoscope 5 to be inserted into, e.g., a large intestine 4 as a subject, a control device 8 including a light source portion 6 which supplies illumination light to the endoscope 5 and a signal processing portion 7, and a monitor 9 for observation which displays a video signal outputted from the signal processing portion 7.

A video signal outputted from the signal processing portion 7 is inputted to the insertion direction detecting device 3, which detects and displays an insertion direction.

The endoscope 5 has an elongated insertion portion 11 to be inserted into the large intestine 4 or the like, an operation portion 12 which is provided at a rear end of the insertion portion 11, and a universal cable 13 extending from the operation portion 12. A connector 14 at an end of the universal cable 13 is detachably connected to the control device 8.

The light source portion 6 in the control device 8 has a lamp 15 which generates illumination light. Illumination light from the lamp 15 is incident on an incident end of a light guide 16 of the endoscope 5. The illumination light incident on the incident end is transmitted to a light guide exit end of a distal end portion 17 of the insertion portion 11. The transmitted illumination light exits from the light guide exit end to illuminate an interior of the large intestine 4, into which the insertion portion 11 is inserted.

At the distal end portion 17, an observation window (image pickup window) is provided adjacent to the light guide exit end. An objective lens 18 and a charge coupled device (abbreviated as a CCD) 19 or the like arranged at an imaging location of the objective lens 18 are arranged at the observation window.

Note that a bendable bending portion 20 is provided at a rear end of the distal end portion 17. An operator such as a surgeon can bend the bending portion 20 in an arbitrary direction, a vertical direction or a horizontal direction, by performing an operation of rotating a bending knob 30 or the like which is provided at the operation portion 12.

The CCD 19 described above is connected to a CCD drive circuit 21 constituting part of the signal processing portion 7 in the control device 8 via a signal line. Upon receipt of a CCD drive signal applied from the CCD drive circuit 21, the CCD 19 outputs image pickup signals obtained after photoelectric conversion.

The image pickup signals are inputted to a signal processing circuit 22. The signal processing circuit 22 generates video signals which are, e.g., analog RGB signals from the image pickup signals.

The video signals are inputted to the monitor 9 for observation. An endoscope image which has been formed on an image pickup surface of the CCD 19 is displayed on a display surface of the monitor 9 for observation. The insertion direction detecting device 3, to which the video signals are inputted, has a configuration as shown in FIG. 2.

The insertion direction detecting device 3 is composed of a computer 23 and a display device 24. Analog ROB signals are inputted to an I/O control portion 26 which performs input-output control via an A/D converter 25 in the computer 23 after being converted into digital RGB signals.

The I/O control portion 26 is connected to a central processing unit (abbreviated as a CPU) 27 which performs image processing for insertion direction detection, a storage device 28 storing a main program 28a for image processing of the CPU 27, and the display device 24. The CPU 27 is also connected to a main memory 29 which is used as a work area when image processing for insertion direction detection is performed and temporarily stores image information and the like.

The main program 28a is a program which performs a series of processes involved in insertion direction detection according to the present embodiment. The main program 28a makes a request of the I/O control portion 26 to acquire an image signal from the A/D converter 25, to display a result of insertion direction detecting processing on the display device 24, or to perform other processes.

In the present embodiment, the CPU 27 has processing facilities as shown in FIG. 3. More specifically, the CPU 27 has a scene feature value computing facility 27a for computing a scene feature value from a scene of an endoscope image and a determination analysis facility (classification facility) 27b for classifying a scene feature value into one of a plurality of different classes for feature values (e.g., lumen dark regions, folds, and others to be described later) classes closely relating to an endoscope insertion direction in a body cavity (i.e., a luminal structure in a body cavity) to detect an endoscope insertion direction, on the basis of a feature value vector of the scene feature value.

The CPU 27 also has an insertion direction computing (detecting) facility 27d for computing an insertion direction for each of the plurality of different feature value classes.

Accordingly, in the present embodiment, even if a plurality of different feature values or structures corresponding to feature values are present in each scene of an endoscope image used when an endoscope insertion direction in the endoscope image is detected, the feature values are classified into groups of feature values, and an insertion direction is computed corresponding to each of the groups, into which the classification is performed. The present embodiment is thus configured to be capable of appropriately computing an insertion direction.

Note that, in the present embodiment, the classification facility 27b includes an essential class computing facility 27c for computing an essential feature value class among a plurality of feature value classes in addition to a facility for classification, as shown in FIG. 3. The process of actually computing an insertion direction is performed only on an essential feature value class, thereby reducing a workload. A case without a reduction in workload will be described later (FIG. 14).

Operation of an (endoscope) insertion direction detecting method according to the present embodiment will be described with reference to the flow chart in FIG. 4.

The CPU 27 of the insertion direction detecting device 3 acquires, e.g., an R image among RGB images of an endoscope image, as shown in step S1, and temporarily stores the R image in the main memory 29 or storage device 28.

In a next step, $S_2$, the CPU 27 performs, on a scene of the acquired R image, a process of computing scene feature values including a lumen dark section and a fold. The scene feature value computing will be described later. Each scene may be each frame in an endoscope image of a moving image or may be one frame in a period of several frames.

In a next step, $S_3$, the CPU 27 performs determination analysis processing on the computed scene feature values.

As the determination analysis processing, for example, one disclosed in Japanese Patent Application Laid-Open Publication No. 2002-165757 can be adopted.

The CPU 27 performs determination analysis involving classifying the computed scene feature values as feature value vectors into a plurality of feature value classes, such as a class of lumen dark sections, a class of folds, and a class of others, closely relating to an endoscope insertion direction (or a luminal structure) using a statistical or nonstatistical discriminator.

After the classification, the CPU 27 computes an indication of the degree of similarity to training data prepared as a reference for each of the feature value classes including the class of lumen dark sections, the class of folds, and the class of others and computes an essential feature value class if there are a plurality of feature value classes containing any member among the feature value classes, as shown in step S4.

The CPU 27 performs a branching process below according to the essential feature value class computed in step S4.

If the class of lumen dark sections is computed as the essential feature value class, the CPU 27 performs, on the R image, a process of detecting a lumen dark section region, as shown in step S5a. The lumen dark section region detecting process is performed by detecting a region of a predetermined size or more using a threshold value for dark section detection. Alternatively, the lumen dark section region detection may be performed using information used in the process in step S2 or S3. Further alternatively, the lumen dark section region detection may be performed using, for example, a dark section region detecting method in Japanese Patent No. 2,710,384.

After the lumen dark section region detection, the CPU 27 displays a lumen dark section marker Ma in a detected lumen dark section region of the endoscope image, as shown in step S6a. Alternatively, the CPU 27 may display an insertion direction marker Ma' facing from a center of the endoscope image toward a lumen dark section direction, as indicated by a dotted line in FIG. 5.

If the class of folds is computed as the essential class in step S4, the CPU 27 performs a process of detecting a fold from the R image, as shown in step S5b. After that, the CPU 27 performs a process of computing a barycentric position of the fold, as shown in step S6b.

The fold detecting and barycentric position computing process can be performed using the information used in the process in step S2 or S3. Alternatively, the barycentric position of the fold may be computed on the basis of a fold detecting and fold barycentric position detecting method in Japanese Patent No. 2,680,111.

As shown in step S7, the CPU 27 obtains a center of a lumen including the fold and displays an insertion direction marker Mb, as shown in FIG. 6.

If the class of others is computed as the essential class (i.e., if a lumen dark section or fold cannot be sufficiently computed from the scene) in step S4, the CPU 27 detects a density gradient from the R image, as shown in step S5c. As the density gradient detecting process, for example, a density gradient detecting method in Japanese Patent Application Laid-Open Publication No. 2003-093328 is adopted. The CPU 27 obtains the density gradient of the endoscope image on the basis of the density gradient detecting method. The CPU 27 displays an insertion direction marker as shown in FIG. 6 in a direction of the detected density gradient.

The branching process involving displaying an insertion direction marker or the like is performed in the above-described manner, and the CPU 27 reaches the end of the branching process in step S8. The CPU 27 returns to the first step, $S_1$, to repeat the same processing for a next scene.

In the present embodiment, as shown in FIG. 4, the CPU 27 performs a process of computing scene feature values in each scene of an endoscope image of a moving image, performing determination analysis on the scene feature values, classifying each scene feature value into the class of lumen dark sections, folds, or others as feature values closely relating to an endoscope insertion direction (i.e., a luminal structure), detecting an insertion direction on the basis of information on an essential feature value class, and displaying information such as an insertion direction marker.

Accordingly, a surgeon can easily lead a distal end side of the insertion portion 11 into a lumen dark section by performing bending operation in accordance with insertion direction information and becomes able to smoothly perform insertion operation.

As described above, the method according to the present embodiment remedies the drawback of the conventional examples of performing insertion direction detection depending on order of extracted or detected feature values and performs high-accuracy insertion direction detection. Additionally, in the present embodiment, the CPU 27 performs process-reducing control such that if classification into a plurality of feature value classes is performed, insertion direction detection is not performed for every group of classified feature values but is performed on an essential feature value class.

That is, the CPU 27 performs computing of an insertion direction corresponding to an essential feature value and display of the computed insertion direction, thereby allowing a reduction in workload.

The scene feature value computing and the scene feature value determination analysis (classification) will be described. In the present embodiment, a scene feature value is computed by computing an autocorrelation coefficient, or more specifically a higher order local autocorrelation coefficient. A description of such a higher order local autocorrelation coefficient is given in, e.g., Hasegawa, "Pattern Recognition for Understanding of Scene," O Plus F, pp. 1130-1136, October 2003 as Non-Patent Document 1.

A method for computing a scene feature value is a method for obtaining a scene feature value of a texture in an image serving as a scene. A method using a higher order local autocorrelation coefficient as a scene feature value is a method for statistically computing a scene feature value by defining an autocorrelation function using up to n points (generally, n=3) within a local region (e.g., a 3×3 pixel region) and applying the autocorrelation function to an entire image.

FIG. 7 shows higher order local autocorrelation features as two-dimensional reference patterns used for scene feature value computing according to the present embodiment. Each feature is characterized by arrangement of a pixel section (pixel sections) indicated by "1" in FIG. 7. The CPU 27 sets a 3×3 pixel region for an R image. The CPU 27 computes a scene feature value by performing a process corresponding to local autocorrelation coefficient computing of adding up pixel values at sections indicated by "1" for each of No. 1 to No. 25 in FIG. 7 while shifting the 3×3 pixel region on the R image by one pixel at a time.

An example in which a feature value for feature No. 2 in FIG. 7 is computed is shown in FIGS. 8 and 9. FIG. 8 shows a first 3×3 local region set at an upper left corner of a certain scene image. To compute a scene feature value for feature No. 2, pixel values a22 and a23 of pixels a22 and a23 (denoted by same reference characters for sake of simplicity) are added up. That is, the CPU 27 computes a sum a22+a23.

The CPU 27 translates the 3×3 local region to a right side by one pixel and sets a 3×3 local region shown in FIG. 9. The CPU 27 adds a sum of the pixel value a23 and a pixel value a24 to the sum obtained in FIG. 8. The above-described process is repeated for all of scene images, thereby computing the scene feature value for feature No. 2. Although only the case of feature No. 2 has been described, same processing is performed for each of the other features. In the manner, 25 scene feature values can be computed.

In the present embodiment, if the 25 features shown in FIG. 7 are used, image reduction processing is performed, as shown in FIG. 10, and scene feature values are computed. With the operation, scene feature value computing processing is speeded up.

FIG. 10 shows scene feature value computing and a process of performing classification using a computed scene feature value as a feature value vector.

As shown in FIG. 10, when scene feature value computing starts, the CPU 27 performs a process of reducing an image, as shown in step S11. In the case, the CPU 27 extracts a part of 512×512 size of an image pickup region of an R image in an endoscope image and reduces the extracted image to, e.g., 32×32 size.

For example, a discrete wavelet transform which is a known technique is used as a reduction method for reducing an image (in other words, performing resolution conversion). FIG. 11 shows transform coefficients (subband images) of decomposition level 2 in a discrete wavelet transform. The subband images generated by the discrete wavelet transform are denoted by HH1, LH1, HL1, HH2, LH2, HL2, and LL2.

For example, HH1 represents an image component obtained by using a high-pass filter both in horizontal and vertical directions, and x in HHx represents a decomposition level of an original image. Additionally, LH, HL, and LL represent an image component obtained by using a low-pass filter in the horizontal direction and a high-pass filter in the vertical direction, an image component obtained by using a high-pass filter in the horizontal direction and a low-pass filter in the vertical direction, and an image component obtained by using a low-pass filter in the horizontal direction and a low-pass filter in the vertical direction, respectively.

The transform coefficients LL2, HL2, LH2, and LL2 are derived by decomposing a transform coefficient LL1 into subbands. Note that, at decomposition level 1, an image before decomposition is decomposed into four transform coefficients HH1, LH1, HL1, and LL1 whose horizontal and vertical sizes are respectively 1/2 times horizontal and vertical sizes of the original image (see FIG. 14).

In the above-described manner, subband image generation by a discrete wavelet transform is performed up to decomposition level 4, thereby generating a 32×32 reduced image.

As shown in step S12, the CPU 27 computes a higher order local autocorrelation coefficient described above.

The CPU 27 regards a sequence of 25 computed scene feature values as feature value vectors and performs determination processing for classifying the feature value vectors into feature value classes including the class of lumen dark sections, the class of folds, and the class of others, as shown in step S13.

When the CPU 27 performs the determination processing for classification, the CPU 27 refers to pieces of training data such as feature value vector distributions for the case of lumen dark sections, the case of folds, and the case of others stored in advance in the storage device 28.

The CPU 27 computes an indication of the degree of similarity to each of the pieces of training data for the case of lumen dark sections, the case of folds, and the case of others. If there are a plurality of feature value classes containing any member, the CPU 27 computes an essential feature value class. The CPU 27 performs the process of detecting an insertion direction for the essential feature value class and displays the detected insertion direction, as described with reference to FIG. 4.

The present embodiment involving the above-described processing computes a scene feature value using an autocorrelation coefficient. Accordingly, even if noise occurs or enters due to a disturbance or the like, it is possible to compute a feature value closely relating to an endoscope insertion direction (or a luminal structure) from each scene with high accuracy without being much affected by noise.

Even if a plurality of structures such as a lumen dark section and a fold are present in an endoscope image, the present embodiment extracts scene feature values, classifies the scene feature values into feature value classes including the class of lumen dark sections and the class of folds, and computes and displays an insertion direction using a processing algorithm corresponding to an essential feature value class.

The present embodiment appropriately computes and displays an insertion direction not only if a structure including only one feature value in a lumen dark section, fold, or the like is present but also if a plurality of structures are present. Accordingly, a surgeon can smoothly perform insertion operation and an endoscopic examination.

A first modification of FIG. 10 will now be described. In FIG. 10, an image is reduced, and a higher order local autocorrelation coefficient is computed for the reduced image. In contrast, in the first modification, the CPU 27 takes a simplified processing approach. More specifically, the CPU 27 computes an average value for pixels in a small region as a scene feature value.

In the present modification, the CPU 27 performs computing of an average value for pixels in a small region, which can also be referred to as resolution conversion of an endoscope image, for scene feature value computing.

FIG. 12 shows a flow chart showing scene feature value computing and the like according to the first modification. When a scene feature value computing process starts, the CPU 27 generates a reduced image in step S31 by dividing a picked-up R image into, e.g., 8×8 small regions and using an average value of pixel values in each small region as a small region pixel value.

In a next step, S32, the CPU 27 regards each small region pixel value in the reduced image as a component of a scene feature value, scans the small region pixel values, and computes the scene feature value with a sequence of the small region pixel values as a feature value vector.

In a next step, S33, the CPU 27 performs determination analysis using the feature value vector.

In the present modification, feature value classification can be performed by simpler processing than the processing method shown in FIG. 10.

A second modification of FIG. 10 will be described with reference to the flow chart shown in FIG. 13. In the present modification, a processing method in which the CPU 27 uses a histogram is adopted.

The present modification adopts a method for comparing a histogram of pixel values or a frequency characteristic of an image with a histogram of a training image in order to compute a scene feature value without depending on rotation and translation.

As for a frequency characteristic, a discrete wavelet transform described above is used.

When scene feature value computing starts, the CPU 27 performs a discrete wavelet transform described above on an R image in a first step, S41.

By step S41, subband images, spectra in three horizontal (HL1), vertical (LH1), and diagonal (HH1) directions and a low-frequency component (LL1) are obtained for each of images at resolutions, as shown in FIG. 14.

In a next step, S42, the CPU 27 computes histograms of the subband images. In a next step, S43, the CPU 27 performs classification by performing histogram comparison. Note that although the case of subband images of decomposition level 1 is described here, subband images of decomposition level 2 may be used instead.

For example, a method using a $\chi^2$ distribution is adopted as a method for histogram comparison. In the case, to perform comparison with K histograms, values of $\chi^2$ distributions are computed by formula (1) below, and comparison values COMP are computed by formula (2) below:

$$\chi^2 = \Sigma_i (q_i - h_i)^2 / (q_i + h_i) \tag{1}$$

$$\text{COMP} = (1/K) \Sigma_\alpha (\chi^2_\alpha) \tag{2}$$

where $\Sigma_\alpha$ represents a sum of $\alpha$ equals 1 to K, $\Sigma_i$ represents a sum of i, $q_i$ is an ith frequency value of a histogram to be compared (detected), and $h_i$ is an ith frequency value of a histogram of a training image.

A histogram of a training image corresponding to feature values in each of feature value classes into which the classification is performed is prepared in advance for the feature value class, and a $\chi^2$ distribution for each feature value class is computed. With the process, it is possible to classify each feature value into a feature value class to which a training image whose $\chi^2$ distribution has a smallest value belongs. It is also possible to compute an essential feature value class to which a training image whose $\chi^2$ distribution has a smallest value belongs.

As described above, according to the present modification, it is possible to compute a feature value such as a lumen dark section relating to an endoscope insertion direction (or a luminal structure) using a histogram. It is also possible to compute an essential feature value and detect an insertion direction for the essential feature value with high accuracy.

Note that a correlation coefficient $(\Sigma_i q_i \cdot h_i - \Sigma_i q_i \cdot \Sigma_i h_i) / ((\Sigma_i q_i^2 - \Sigma_i q_i \cdot \Sigma_i q_i) \cdot (\Sigma_i h_i^2 - \Sigma_i h_i \cdot \Sigma_i h_i))$ or a difference $\Sigma_i \min(q_i, h_i)$ may be used instead of a $\chi^2$ distribution.

As described above, even in each modification, it is possible to compute a feature value relating to an endoscope insertion direction (or a luminal structure) and detect an insertion direction with high accuracy.

Second Embodiment

A second embodiment of the present invention will be described with reference to FIGS. 15 to 20. In the first embodiment, classification of scene feature values is performed after determination analysis of the feature values, and an essential class is computed at the time of the classification. In the present embodiment, a branching process is performed according to a classification result instead of the essential class computing process.

Figure 15:
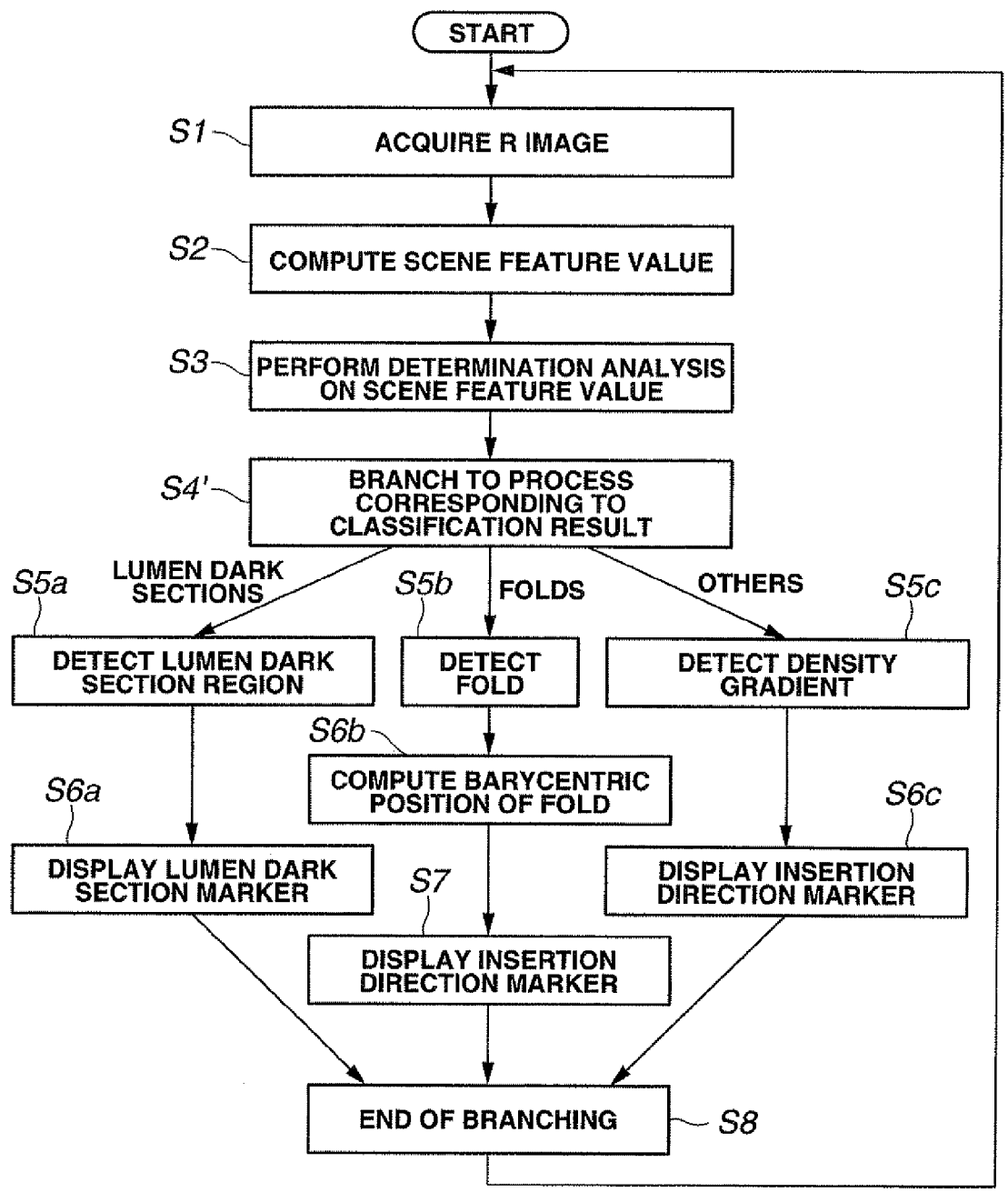
FIG. 15 is a flow chart showing an endoscope insertion direction detecting process according to a second embodiment of the present invention.
Figure 17:
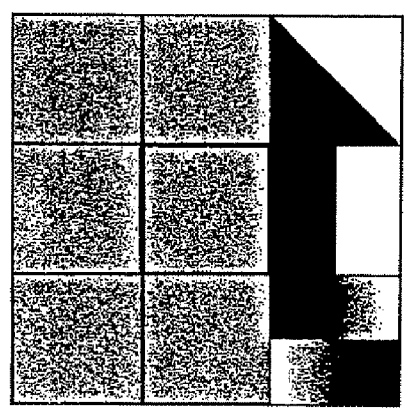
FIG. 17 is a second view for explaining a case where images surrounding an image at a certain resolution are merged into the image and the like, according to the second embodiment of the present invention.

FIG. 15 shows an endoscope insertion direction detecting method according to the present embodiment. In FIG. 17, step S4' for branching to a process corresponding to a classification result replaces the essential class computing in step S4 of FIG. 4.

Accordingly, in the present embodiment, if a plurality of structures corresponding to respective feature values are present, a plurality of insertion directions are detected corresponding to the plurality of feature values, and a detection result is displayed. In the case, if the plurality of insertion directions are all identical to each other, insertion direction detection accuracy is high. If the plurality of insertion directions are different from each other, the insertion direction detection accuracy is lower than the case where the detected insertion directions are all identical to each other. In the case, a surgeon determines an insertion direction from display contents.

Accordingly, the present embodiment overcomes the conventional disadvantage that a result of detecting an insertion direction is affected by order of feature value detection (extraction) if a plurality of structures corresponding to respective feature values are present in a scene.

Note that, as a modification of the present embodiment information on a value of an indication of the degree of similarity to training data prepared in advance may be reflected in display of an insertion direction, as described in the first embodiment. For example, size of an arrow indicating an insertion direction may be changed according to magnitude of the value of the indication, and a surgeon may be notified that an insertion direction indicated by a largest arrow is an insertion direction detected with highest accuracy.

A detection method according to the present embodiment for detecting, with high accuracy, a region of a lumen dark section (for insertion direction detection) in a case where a feature value class of lumen dark sections is detected by feature value classification which can also be applied to the first embodiment will be described below.

Lumen dark section region detection according to the present embodiment is an improvement over the contents described in Japanese Patent No. 2,710,384. The improvement here will be briefly described below.

The method described in Japanese Patent No. 2,710,384 performs region division and merging by generating multiple images different in resolution and comparing brightness average values between upper and lower floors and detects a dark section region with a predetermined brightness range.

However, it is difficult for the method to detect a boundary of a dark section with a smooth brightness change. Additionally, since the method compares only brightness average values, the method may erroneously detect a small region with wide dispersion or a small region with a texture.

Figure 16:
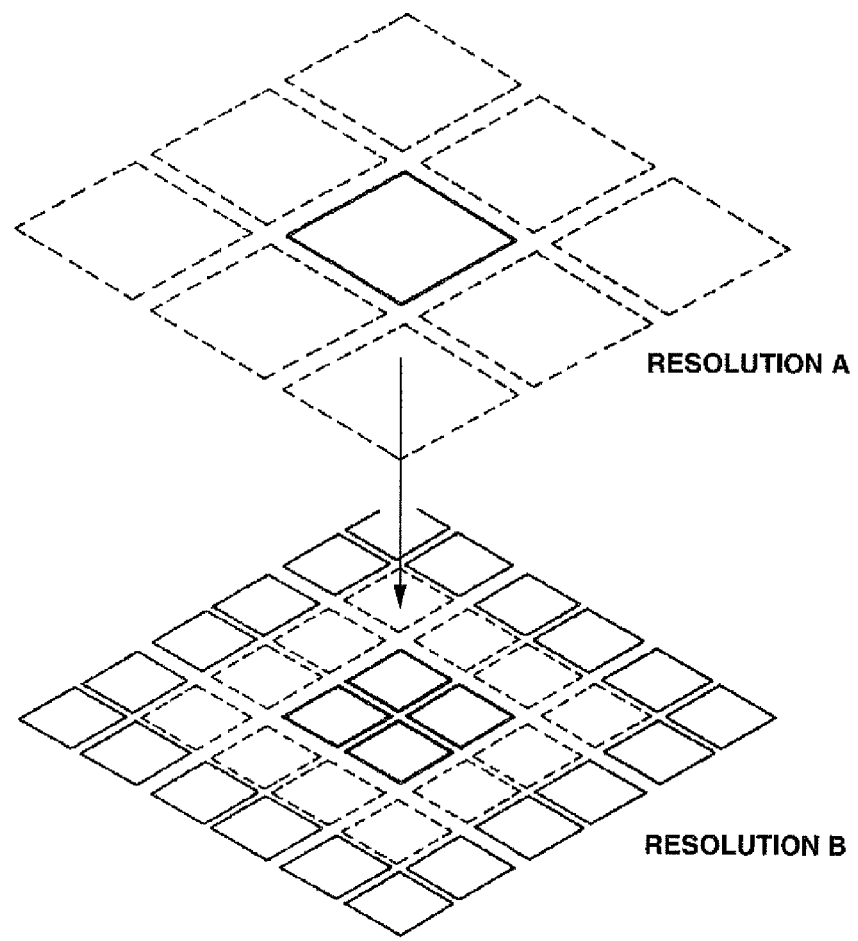
FIG. 16 is a first view for explaining a case where images surrounding an image at a certain resolution are merged into the image and the like, according to the second embodiment of the present invention.

More specifically, if a difference or ratio between a pixel value (an average value for pixels within a small rectangular region in an original image) of pixels (the small region) indicated by a solid line at a resolution A detected as a lumen dark section region, as shown in FIG. 16, and a pixel value of adjacent pixels (small regions indicated by dotted lines at the resolution A is at or below a predetermined threshold value, the method described in the above publication merges the small regions.

The method merges adjacent small regions in an image at a next lower floor using multiple images different in resolution in a four-branching quadtree structure and obtains an outline of a lumen dark section region.

More specifically, if a difference or ratio between a pixel value of pixels located at a same position as the pixels of the lumen dark section region at the resolution A (four small regions indicated by thick solid lines at a resolution B) and a pixel value of adjacent pixels indicated by dotted lines (small regions indicated by the dotted lines at the resolution B) in an image at a next lower floor (an image at the resolution B at a floor lower than the resolution A, as shown in FIG. 17) is at or below a predetermined threshold value, the method merges the small regions.

As described above, in the method in the above publication, an average value of pixel values of part of an original image within a small region as which pixels are regarded is used as a pixel value at each of the resolutions A and B.

However, if an edge or texture is present within a small region or if a density gradient is present, as shown in FIG. 17, accurate determination is impossible, and an erroneous lumen dark section region may be extracted. For example, average values of pixel values in three small regions on a right side in FIG. 17 are all same. Accordingly, the above method may perform a process of merging the regions with the same average values and extract an erroneous lumen dark section region.

For the reason, the present embodiment is configured to appropriately perform merging processing without erroneous extraction (erroneous merging) as in FIG. 17. Accordingly, a CPU 27 according to the present embodiment performs processes as in FIGS. 18 and 19.

Figure 18:
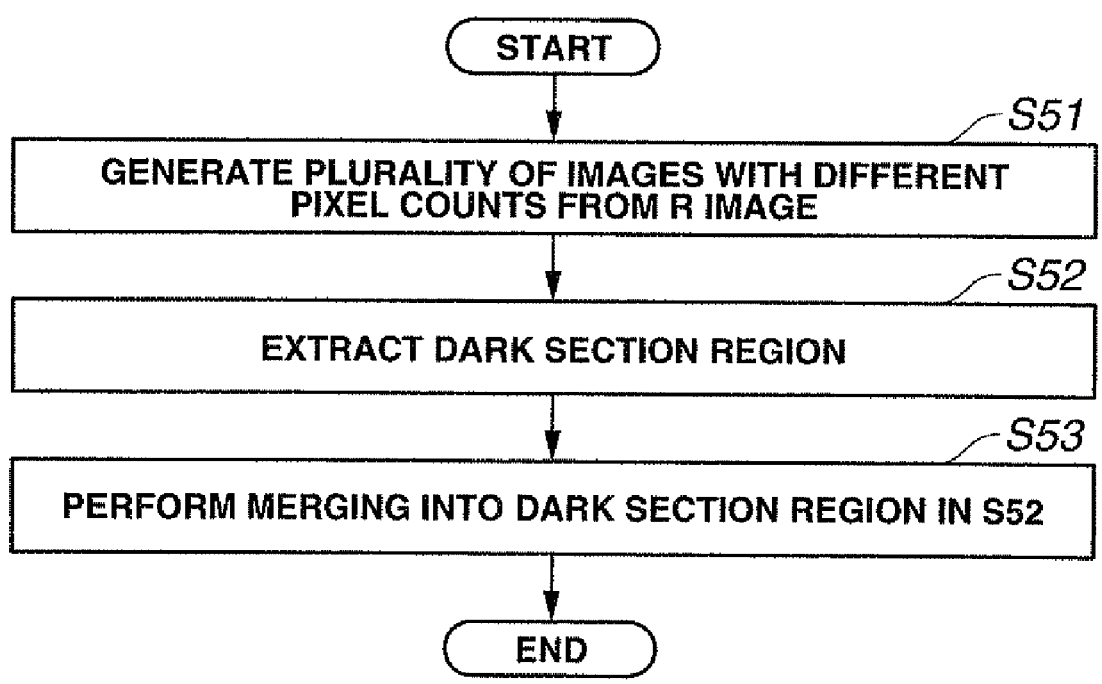
FIG. 18 is a flow chart showing an overview of a procedure for a process of detecting a dark section region according to the second embodiment of the present invention.

When lumen dark section detection starts, the CPU 27 generates a plurality of images different in pixel count from an acquired R image, in step S51 of FIG. 18.

In a next step, S52, the CPU 27 examines brightness of each pixel in each of the plurality of images generated in the previous step, S51, in increasing order of pixel count and extracts a dark section region corresponding to a lumen dark section in an image with a predetermined pixel count.

In a next step, S53, the CPU 27 performs merging processing for merging a region which is adjacent to the dark section region obtained in the previous step, S52, and is within a desired brightness range into the dark section region obtained in the previous step, S52. In the above-described manner, the CPU 27 performs the processes in step S51 to S53, thereby detecting a dark section region corresponding to a lumen dark section.

Figure 19:
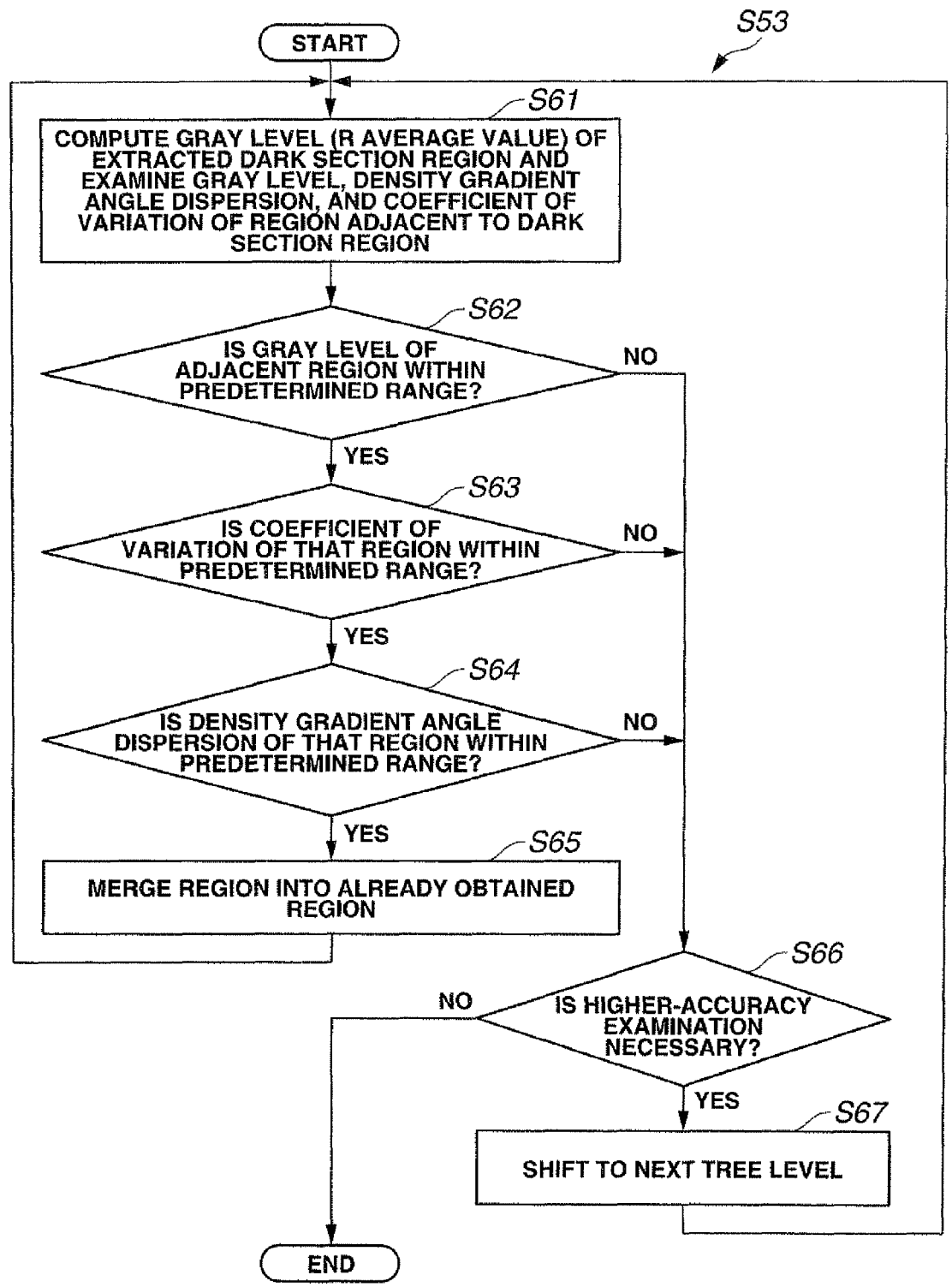
FIG. 19 is a flow chart showing details of a procedure for a process in step S53 of FIG. 18 according to the second embodiment of the present invention.

Details of step S53 in the present embodiment are shown in FIG. 19. When the process in step S53 starts, the CPU 27 computes a gray level (R average value) of the extracted dark section region in step S61. In the case, the CPU 27 computes an R average value in the dark section region (extracted in the previous step, S52) indicated by the solid line in the image at the resolution A, as shown in, e.g., FIG. 16, as a gray level in the dark section region.

The CPU 27 also computes a gray level (i.e., an R average value), density gradient angle dispersion, and a coefficient of variation (C. V.: a value obtained by dividing a standard deviation by an average value) in each of the regions adjacent to the dark section region (e.g., the regions surrounded by the dotted lines at the resolution A in FIG. 16).

Figure 20:
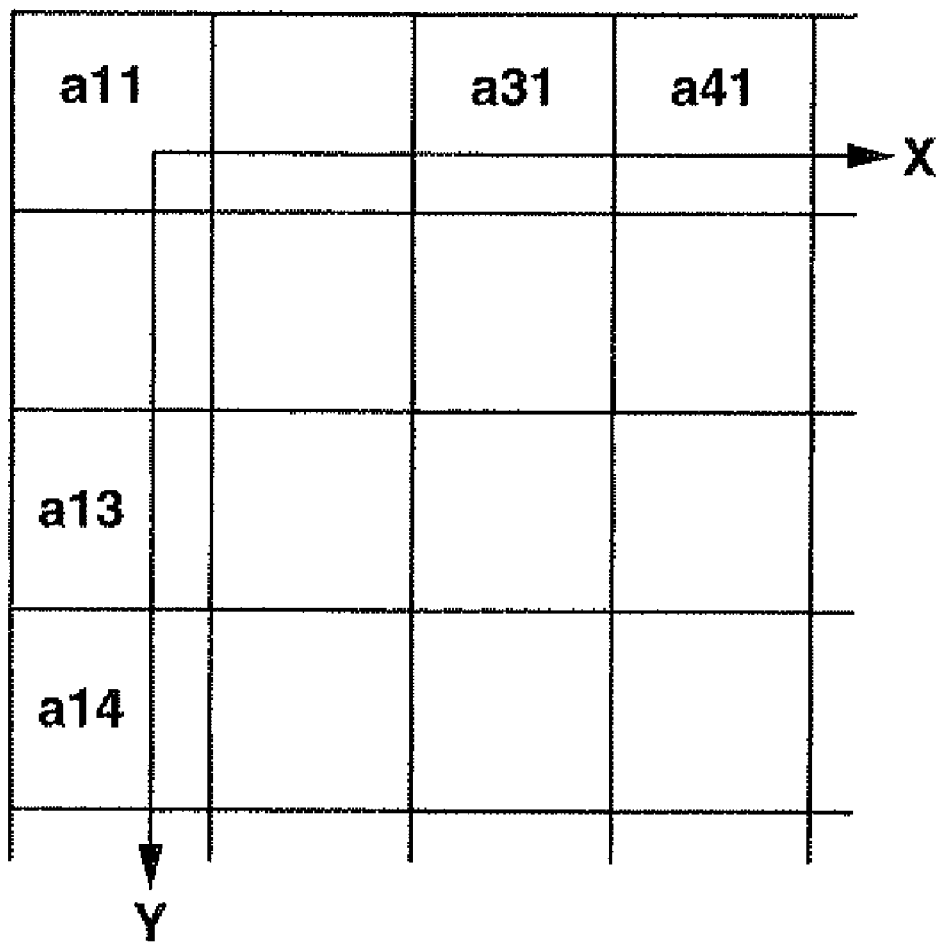
FIG. 20 is a view for explaining computing of a density gradient angle according to the second embodiment of the present invention.

A density gradient angle is obtained using a tangent of an X-direction gray gradient and a Y-direction gray gradient on the basis of a gray value gradient of each of third pixels with respect to a pixel a11 in a 3×3 small region as a target or information on a difference between the pixels, as shown in FIG. 20.

More specifically, if pixels are as shown in FIG. 20, a density gradient angle θ is computed by θ=arc tan(a31−a11)/(a13−a11). Density gradient angle dispersion is density gradient angle dispersion at a position of a pixel included in a region.

In a next step, S62, the CPU 27 examines whether a difference or ratio between the gray level in the extracted region and the gray level of each adjacent region is within a predetermined range. If the difference or ratio is within the predetermined range, the CPU 27 advances to a next step, S63. On the other hand, if the difference or ratio is outside the predetermined range, the CPU 27 shifts to a process in step S66.

In the next step, S63, the CPU 27 examines whether the coefficient of variation of each adjacent region is within a predetermined range. If the coefficient of variation of the adjacent region is within the predetermined range, the CPU 27 advances to a next step, S64. On the other hand, if the coefficient of variation of the adjacent region is outside the predetermined range, the CPU 27 shifts to the process in step S66.

In the next step, S64, the CPU 27 examines whether the density gradient angle dispersion of each adjacent region is within a predetermined range. If the density gradient angle dispersion of the adjacent region is within the predetermined range, the CPU 27 advances to a next step, S65. On the other hand, if the density gradient angle dispersion of the adjacent region is outside the predetermined range, the CPU 27 shifts to the process in step S66.

If the conditions in steps S62 to S64 are met, the CPU 27 merges the adjacent surrounding regions into the already obtained dark section region in step S65 and returns to step S61.

On the other hand, if any of the conditions shown in steps S62 to S64 is not met, the CPU 27 determines from a set value for a current resolution whether higher-accuracy examination is necessary, as shown in step S66. If the set value for the current resolution is identical to a set value for a predetermined terminal resolution, the CPU 27 ends the process. Otherwise, the CPU 27 performs same processing on an image at a next tree level (resolution). For example, if determination processing has been performed at the resolution A in FIG. 16, the CPU 27 performs the same determination processing for the resolution B below the resolution A. After that, the CPU 27 returns to step S61.

According to the present embodiment, the above-described process is recursively performed on a dark section region corresponding to an initial lumen dark section, thereby expanding a lumen dark section region and improving accuracy of an outline of the lumen dark section region.

As described above, according to the present embodiment, in the process of merging adjacent regions, comparison is performed in consideration of not only an average pixel value for each adjacent region but also variations in pixel value between adjacent regions. This leads to merging of regions with almost uniform pixel value distributions and makes it possible to improve lumen dark section region detection accuracy.

According to the present embodiment, in the process of merging adjacent regions, comparison with density gradient angle distribution of each adjacent region is performed. This leads to merging of regions with a smooth gradient and makes it possible to improve lumen dark section region detection accuracy.

Since the above-described merging processing is performed, erroneous merging, which refers to performing merging even when a gray level simply falls within a predetermined range, as shown in, e.g., FIG. 17, is prevented, and a lumen dark section region can be detected with high accuracy. Accordingly, according to the present embodiment, an improvement in lumen dark section region detection accuracy improves endoscope insertion direction detection accuracy.

Third Embodiment

A third embodiment of the present invention will be described with reference to FIGS. 21 to 25. The present embodiment provides a method for detecting a lumen dark section with high accuracy, as in the second embodiment. A method for detecting a lumen dark section according to the present embodiment is shown in a flow chart in FIG. 21. The method is an improvement over a method disclosed in, e.g., Japanese Patent Application Laid-Open Publication No. 2003-93328.

It is difficult for the method disclosed in Japanese Patent Application Laid-Open Publication No. 2003-93328 as a conventional example to detect a lumen dark section region C to be detected with high accuracy if a dark section region D is present in addition to the lumen dark section region C as in, e.g., an endoscope image shown in FIG. 22. Note that, in the example, a bright region including a bent intestine and a fold and a dark region E are deep in the lumen dark section region C.

A density value along a line segment F-F' connecting the lumen dark section region C and the dark section region D in FIG. 22 is shown in FIG. 23.

In the above conventional example, it is necessary to uniquely determine a threshold value for detecting the lumen dark section region C. As a determination method, analysis of a histogram of pixel values within an entire screen or the like is widely used.

If the determined threshold value is T, only the region E in FIG. 22 can be extracted. If the determined threshold value is T', part of the dark section region D is extracted. As described above, the conventional example needs to determine an optimum threshold value for each image and has difficulty in detecting the lumen dark section region C with high accuracy.

Figure 21:
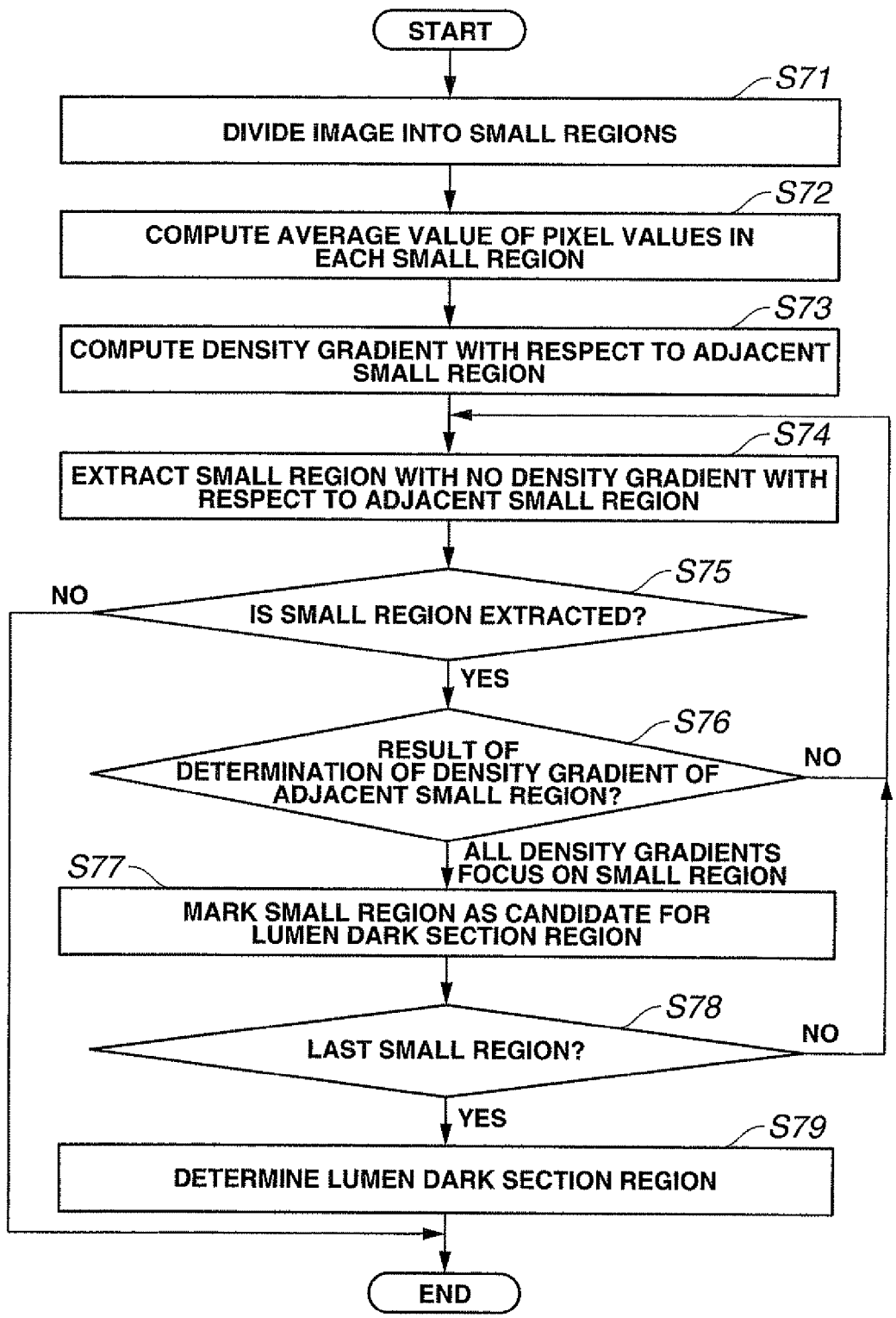
FIG. 21 is a flow chart showing a lumen dark section region detecting process according to a third embodiment of the present invention.

For the reason, the present embodiment extracts the lumen dark section region C by the detection method indicated by the flow chart shown in FIG. 21. The detection method is a method for extracting only the lumen dark section region C in FIG. 22.

Figure 25:
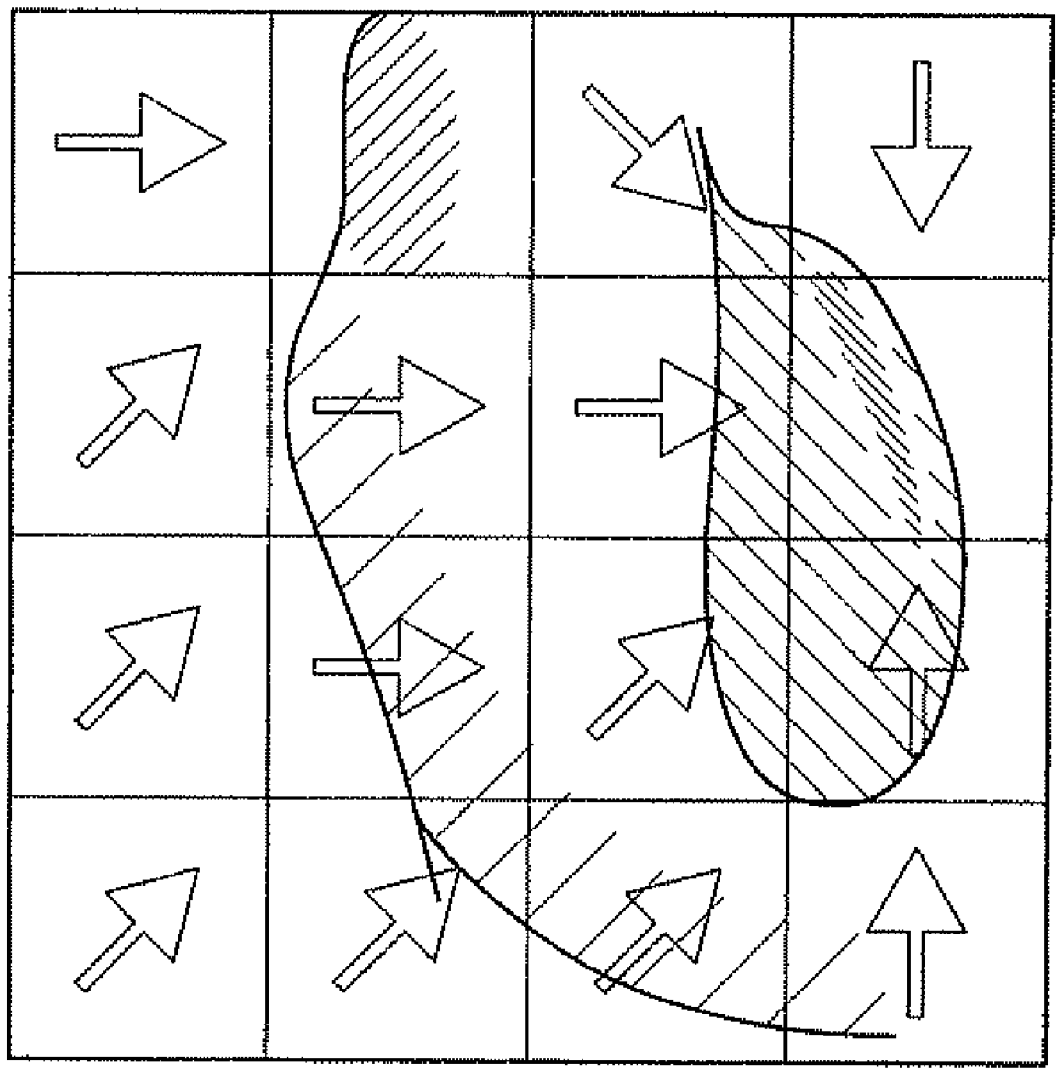
FIG. 25 is a view showing density gradient directions in the endoscope image shown in FIG. 22 according to the method in FIG. 21, according to the third embodiment of the present invention.

As shown in FIG. 21, a CPU 27 divides an endoscope image into small regions in a first step, S71. The present embodiment will describe an example in which an endoscope image is divided into 4×4 small rectangular regions bxy (x=1 to 4, y=1 to 4), as shown in FIG. 25, for sake of simplicity.

In a next step, S72, the CPU 27 computes an average value <bxy> of pixel values of each small region bxy. In the present embodiment, an average value of R color signals of RGB color signals corresponding to an endoscope image is computed.

In a next step, S73, the CPU 27 compares, for each small region bxy, an average value of values of pixels adjacent in each of eight directions (or three directions in the case of a small region at each corner or five directions in the case of a small region along a perimeter) with the average value <bxy> of pixel values of the small region bxy to be processed (or computes a difference value) and computes a density gradient direction. If the average value <bxy> of the pixel values of the small region bxy is smaller than the average values <bxy> for adjacent small regions to be compared, the density gradient direction has a value of 0.

More specifically, in the case of a first small region b11, a direction corresponding to one of difference values <b21>−<b11>, <b22>−<b11>, and <b12>−<b11> which is negative and has a largest absolute value is determined as a density gradient direction.

In the case of the small region b11, since an average value <b21> is smallest, a density gradient direction is a direction from the small region b11 toward a small region b21. In the manner, information on a density gradient direction distribution (array) as shown in FIG. 25 is obtained.

Note that if computed difference values as described above are all positive, a density gradient direction is 0 as described above. Each of the small region b21 and a small region b42 in FIG. 25 (see FIG. 24 for reference characters b21 and the like) has a density gradient direction=0.

In a next step, S74, the CPU 27 sequentially extracts small regions with no density gradient with respect to adjacent small regions, i.e., with a density gradient direction=0.

In a next step, S75, the CPU 27 determines whether any small region with no density gradient is extracted in the process in step S74. If no such small region is extracted, the CPU 27 ends the process. On the other hand, if any small region is extracted, the CPU 27 advances to a process in step S76.

In the process in step S76, the CPU 27 determines, for each of the small regions with no density gradient (with a density gradient direction=0), whether density gradients of all of small regions adjacent to the small region intensively point toward one small region.

As for, e.g., the small region b21 in FIG. 25, density gradients of lower, lower right, and right adjacent small regions do not point toward the small region b21. For the reason, the CPU 27 regards a result of the determination in step S76 as N and returns to step S74.

In contrast, as for a small region b42, density gradients of all adjacent small regions intensively point toward the small region b42. If density gradients of all adjacent small regions intensively point toward one small region, the CPU 27 marks the small region as a candidate for a lumen dark section region, as shown in step S77.

In the case of the endoscope image in FIG. 25, the small region b42 is marked as a candidate for a lumen dark section region. In step S78, the CPU 27 determines whether a current small region is a last small region of the small regions with no density gradient. If the current small region is not a last small region, the CPU 27 returns to step S74. On the other hand, if a last small region has been reached, the CPU 27 advances to step S79.

In step S79, the CPU 27 determines a final lumen dark section region among marked candidates for a lumen dark section region. A plurality of small regions can be marked as candidates for a lumen dark section region. In the case, the CPU 27 determines, as a lumen dark section region, one of the candidates for a lumen dark section region which has a smallest average pixel value.

Although an image is divided into 4×4 small rectangular regions in the present embodiment, even if processing is performed using, e.g., non-rectangular regions in a Voronoi diagram or a region obtained as a result of unifying regions of multiple images different in resolution, as in Japanese Patent No. 2,710,384, advantages which suit an object of the present embodiment are achieved.

In the present embodiment, an image is divided into small regions, a density gradient of a small region adjacent to each divided small region is examined, and a small region toward which density gradients point intensively is regarded as a candidate for a lumen dark section region, thereby allowing correct detection of a lumen dark section region without use of a threshold value. Accordingly, according to the present embodiment, endoscope insertion direction detection accuracy is improved.

If determination as to whether all the density gradients intensively point toward one small region is performed in the determination in step S76 in FIG. 21, and a result of the determination shows that there is no corresponding small region, a message may be displayed to the effect that a small region toward which a largest number of density gradients point may be a candidate for a lumen dark section.

According to a configuration of an endoscope insertion direction detecting device of the present invention described in each of the above-described embodiments, even in the case of a scene in which a plurality of feature values relating to an endoscope insertion direction are present, it is possible to detect an insertion direction with high accuracy.

According to a configuration of an endoscope insertion direction detecting method of the present invention including the above-described steps, even in the case of a scene in which a plurality of feature values relating to an endoscope insertion direction are present, it is possible to detect an insertion direction with high accuracy.

In other words, according to the present invention, even in the case of a scene in which a plurality of feature values relating to an endoscope insertion direction, it is possible to detect an insertion direction with high accuracy.

More specifically, according to the present invention, a scene feature value in a scene of an endoscope image picked up by an endoscope inserted into a body cavity is computed, the scene feature value is classified into one of feature value classes including the class of lumen dark sections and the class of folds relating to an endoscope insertion direction, and an insertion direction corresponding to the classified feature value is detected. With the configuration, even in the case of an endoscope image in which a plurality of feature values are present, it is possible to detect an insertion direction with high accuracy.

The present invention is not limited to the above-described embodiments, and various changes may be made without departing from spirit and scope of the invention.

What is claimed is:

1. An endoscope insertion direction detecting device comprising:
   a scene feature value computing section for computing a specific feature value on a scene of an endoscope image of a moving image picked up by an endoscope inserted into a body cavity;
   a classification section for computing a degree of similarity between the scene of the endoscope image and a plurality of training data as references for a plurality of classes, which are respectively defined for different structures in the body cavity, from the specific feature value and the plurality of training data, and classifying the scene of the endoscope image into one or more of the plurality of classes based on the degree of similarity computed; and
   an insertion direction computing section for computing an insertion direction of the endoscope corresponding to the scene of the endoscope image, with respect to the one or more of the classes into which the scene of the endoscope image is classified,
   wherein:
   the classification section performs classification into classes of lumen dark sections, folds, and others as a plurality of specific feature values, and
   if the scene of the endoscope image is classified into the class of lumen dark sections, the insertion direction computing section computes a region of a lumen dark section based on red image components in the endoscope image, if the scene of the endoscope image is classified into the class of folds, the insertion direction computing section computes a barycentric position of a fold based on the red image components in the endoscope image, and if the scene of the endoscope image is classified into the class of others, the insertion direction computing section computes a density gradient in the endoscope image.

2. The endoscope insertion direction detecting device according to claim 1, wherein if the scene of the endoscope image is classified into more than one of the classes, the insertion direction computing section computes an insertion direction of the endoscope only for an essential class among the more than one of the classes into which the scene of the endoscope image is classified.

3. The endoscope insertion direction detecting device according to claim 1, wherein the scene feature value computing section computes an autocorrelation coefficient of the scene of the endoscope image using a plurality of reference patterns.

4. The endoscope insertion direction detecting device according to claim 1, wherein the scene feature value computing section computes a histogram in the scene of the endoscope image.

5. The endoscope insertion direction detecting device according to claim 1, wherein the scene feature value computing section computes the specific feature value based on images of small regions into which the scene of the endoscope image is divided.

6. The endoscope insertion direction detecting device according to claim 1, wherein the scene feature value computing section computes the specific feature value based on a converted image obtained by converting a resolution of the scene of the endoscope image.

7. An endoscope insertion direction detecting method comprising:
a scene feature value computing step of computing a specific feature value on a scene of an endoscope image of a moving image picked up by an endoscope inserted into a body cavity;
a classification step of computing a degree of similarity between the scene of the endoscope image and a plurality of training data as references for a plurality of classes, which are respectively defined for different structures in the body cavity, from the specific feature value and the plurality of training data, and classifying the scene of the endoscope image into one or more of the plurality of classes based on the degree of similarity computed; and
an insertion direction computing step of computing an insertion direction of the endoscope corresponding to the scene of the endoscope image, with respect to the one or more of the classes into which the scene of the endoscope is classified,
wherein the classification step performs classification into classes of lumen dark sections, folds, and others as a plurality of feature values, and if the scene of the endoscope image is classified into the class of lumen dark sections, the insertion direction computing step computes a region of a lumen dark section based on red image components in the endoscope image, if the scene of the endoscope image is classified into the class of folds, the insertion direction computing step computes a barycentric position of a fold based on the red image components in the endoscope image, and if the scene of the endoscope image is classified into the class of others, the insertion direction computing step computes a density gradient in the endoscope image.

8. The endoscope insertion direction detecting method according to claim 7, further comprising an insertion direction display step of making an output for displaying the insertion direction of the endoscope in accordance with the degree of similarity to a display step of displaying the insertion direction of the endoscope in the scene of the endoscope image.

9. The endoscope insertion direction detecting device according to claim 1, wherein if the scene of the endoscope image is classified into more than one of the classes, the insertion direction computing section computes a plurality of insertion directions of the endoscope for more than one of the classes into which the scene of the endoscope is classified.

10. The endoscope insertion direction detecting device according to claim 1, further comprising an insertion direction display output section for making an output for displaying the insertion direction of the endoscope in accordance with the degree of similarity to a display section for displaying the insertion direction of the endo scope in the scene of the endoscope image.

11. An endoscope insertion direction detecting device comprising:
a scene feature value computing section for computing a specific feature value on a scene of an endoscope image of a moving image picked up by an endoscope inserted into a body cavity;
a classification section for computing a degree of similarity between the scene of the endoscope image and a plurality of training data as references for a plurality of classes, which are respectively defined for different structures in the body cavity, from the specific feature value and the plurality of training data, and classifying the scene of the endoscope image into one or more of the plurality of classes based on the degree of similarity computed;
an insertion direction computing section for computing an insertion direction of the endoscope corresponding to the scene of the endoscope image, with respect to the one or more of the classes into which the scene of the endoscope image is classified, and
an insertion direction display output section for making an output for displaying the insertion direction of the endoscope in accordance with the degree of similarity to a display section for displaying the insertion direction of the endoscope in the scene of the endoscope image,
wherein:
if the scene of the endoscope image is classified into more than one of the classes, the insertion direction computing section computes a plurality of insertion directions of the endoscope for more than one of the classes into which the scene of the endoscope is classified,
the classification section performs classification into classes of lumen dark sections, folds, and others as the plurality of specific feature values, and
if the scene of the endoscope image is classified into the class of lumen dark sections, the insertion direction computing section computes density gradients with respect to small regions into which the scene of the endoscope image is divided based on gradients or differences of gray values in adjacent small regions, and designates a small region toward which density gradients of all adjacent small regions point intensively as a candidate for a lumen dark section.

12. The endoscope insertion direction detecting method according to claim 7, wherein if the scene of the endoscope image is classified into more than one of the classes, the insertion direction computing step computes a plurality of insertion directions of the endoscope for more than one of the classes into which the scene of the endoscope is classified.

13. The endoscope insertion direction detecting method according to claim 7, wherein if the scene of the endoscope image is classified into more than one of the classes, the insertion direction computing step computes an insertion direction of the endoscope with respect to only an essential class among more than one of the classes into which the scene of the endoscope image is classified.

14. The endoscope insertion direction detecting method according to claim 7 wherein if the scene of the endoscope image is classified into the class of lumen dark sections, the insertion direction computing step computes density gradients with respect to small regions into which the scene of the endoscope image is divided based on gradients or differences of gray values in adjacent small regions, and designates a small region toward which density gradients of all adjacent small regions point intensively, as a candidate for a lumen dark section.

* * * * *